US012714703B2

(12) United States Patent
Berkowitz

(10) Patent No.: US 12,714,703 B2
(45) Date of Patent: Aug. 25, 2026

(54) WOUND TREATMENT

(71) Applicant: Marie's Original Formulas LLC, Pearl River, NY (US)

(72) Inventor: Freida Berkowitz, Brooklyn, NY (US)

(73) Assignee: Marie's Original Formulas LLC, Pearl River, NY (US)

( * ) Notice: Subject to any disclaimer, the term of this patent is extended or adjusted under 35 U.S.C. 154(b) by 0 days.

(21) Appl. No.: 18/400,006

(22) Filed: Dec. 29, 2023

(65) Prior Publication Data

US 2025/0213551 A1 Jul. 3, 2025

(51) Int. Cl.

*A61K 31/473* (2006.01)
*A61K 9/00* (2006.01)
*A61K 9/16* (2006.01)
*A61K 33/30* (2006.01)

(52) U.S. Cl.

CPC .......... *A61K 31/473* (2013.01); *A61K 9/0014* (2013.01); *A61K 9/1652* (2013.01); *A61K 33/30* (2013.01)

(58) Field of Classification Search

CPC ............ A61K 47/02; A61K 8/02; A61P 17/02
See application file for complete search history.

(56) References Cited

U.S. PATENT DOCUMENTS

2007/0224271 A1* 9/2007 Marraccini ......... A61L 26/0019 424/484
2013/0060208 A1* 3/2013 Givskov ................. A61P 17/02 514/203
2014/0276493 A1* 9/2014 Leung .................... A61K 36/54 424/641
2016/0081968 A1* 3/2016 Svensson ................. A61K 9/06 424/618

FOREIGN PATENT DOCUMENTS

JP 6847569 B2 * 3/2021

OTHER PUBLICATIONS

Buret (Canadian Journal of Veterinary Research, Jan. 2010, vol. 74, pp. 1-10) (Year: 2010).*
Reinhardt et al (Wounds, a Compendium of Clinical Research and Practice, Aug. 2005, vol. 17, pp. 213-221) (Year: 2005).*
Bakhtar (Iran Journal of Public Health, Nov. 2013, vol. 42, pp. 1327-1328) (Year: 2013).*
Lee et al (Frontiers in Pharmacology, Oct. 2019, vol. 10, pp. 1-10) (Year: 2019).*
Quora (Is it okay to apply powder after moisturizer? 2024 with postings from 4, 6 or 7 years before Mar. 2024, https://www.quora.com/Is-it-okay-to-apply-powder-after-moisturizer) (Year: 2024).*
Khalil et al (Royal Society of Chemistry, 2017, vol. 7, pp. 32669-37681) (Year: 2017).*
Ranzato et al (Journal of Ethnopharmacology, 2011, vol. 134, pp. 443-449) (Year: 2011).*
JP-6847569-B2 (Google English translation, downloaded Mar. 2024) (Year: 2024).*
Pramod et al (Natural Product Communications, 2010, vol. 5, pp. 1999-2006) (Year: 2010).*
LibreTexts Chemistry (4.1: Molecular weight of polymers, https://chem.libretexts.org/Bookshelves/Organic_Chemistry/Polymer_Chemistry_(Schaller)/04%3A_Polymer_Properties/4.01%3A_Molecular_Weight ; Downloaded Nov. 2024) (Year: 2024).*
SciTechDaily (Scientists Create the Impossible: New Compound Challenges Fundamental Principle of Chemistry, Jul. 2025, https://scitechdaily.com/scientists-create-the-impossible-new-compound-challenges-fundamental-principle-of-chemistry/) (Year: 2025).*
Chandan K. Sen, "Human Wound and Its Burden: Updated 2020 Compendium of Estimates," Wound Healing Society, Feb. 14, 2021.
Harris-Tryon et al., "Microbiota and Maintenance of Skin Barrier Function," https://www.science.org/doi/10.1126/science.abo0693, Dec. 21, 2023.
Swaney et al., "Living in Your Skin: Microbes, Molecules, and Mechanisms," American Society for Microbiology, Apr. 2021.
Linehan et al., "Non-classical Immunity Controls Microbiota Impact on Skin Immunity and Tissue Repair," Elsevier Inc., Feb. 8, 2018.
Thiboutot et al., "Keeping the peace: commensal Cutibacterium acnes trains CD4+ TH17 cells to trap and kill," https://doi.org/10_1172/JC1145379, 2021.
Alakomi et al., "Lactic Acid Permeabilizes Gram-Negative Bacteria by Disrupting the Outer Membrane," Applied and Environmental Microbiology, May 2000.
Lin et al., "Zinc in Wound Healing Modulation," www.mdpi.com/joumal/nutrients, 2018.
Reinhardt et al., "A Topical Wound Disinfectant (Ethacridine Lactate) Differentially Affects the Production of Immunoregulatory Cytokines In," HMP Global, 2024.
Canchy et al., "Wound Healing and Microbiome, An Unexpected Relationship," https://doi.org/10.1111/jdv.18854, 2023.

(Continued)

*Primary Examiner* — Mark V Stevens
(74) *Attorney, Agent, or Firm* — Weiss & Arons LLP

(57) ABSTRACT

Compositions and methods for wound treatment. Compositions may be formulated as a dry powder. Compositions may include an antibiotic and a metal-containing species. Each of the antibiotic and the metal-containing species may positively modulate wound bed and peri-lesional cellular processes supportive of healing. Methods may include a two-step protocol. The first protocol step may be spreading upon a wound surface an emollient-rich mixture of low-and high-molecular weight (MW) non-water-soluble ingredients of an anti-microbial ointment, forming an occlusive cover over the wound. The second protocol step may be to apply the compositions onto the cover. Low-MW emollients may migrate into, and solubilize components of, the dry powder. The solubilized components and the low-MW emollients may transport below the cover to the wound bed to facilitate effective wound healing. Initial testing and use studies have yielded good wound closures, with minimal-to-no scarring and high regain of function of repaired tissues.

24 Claims, No Drawings

(56) References Cited

OTHER PUBLICATIONS

"Fourteenth Annual Meeting and Exhibition of the Wound Healing Society," Wound Repair and Regeneration, 2004.

Pasquet et al., "The Contribution of Zinc Ions to the Antimicrobial Activity of Zinc Oxide," Elsevier B.V., Sep. 2014.

* cited by examiner

WOUND TREATMENT

FIELD OF TECHNOLOGY

Aspects of the disclosure relate to treatment of wounds. In particular, the disclosure provides compositions of treatments, and methods for treatment, of a variety of open-wound types (e.g., burns, diabetic ulcers, surgical excisions) and across a wide arc of wound healing stages.

BACKGROUND OF THE INVENTION

Open wounds may cause patients discomfort, disfigurement, severe pain and even death. However, open wounds present significant treatment challenges to wound care clinicians. Some particularly difficult challenges may directly contribute, as per analysis of a 2014 United States data set, to approximately 8,200,000 Medicare beneficiaries suffering from chronically non-healing/non-closing open wounds. (Sen CK (2021) Human Wound and Its Burden: Updated 2020 Compendium of Estimates. *Advances In Wound Care* 10:281-292) While difficult-to-treat open wounds such as diabetic foot ulcers and skin lesions from venous deficit may be predominant in the Medicare-age elderly population, challenging open wound sites such as from surgical excision, moderate-to-severe burns, and lacerations (from, e.g., home/work/recreation accidents; disaster/terror/combat wounds) are prevalent throughout all age demographics. As nations' populations expand and/or age, effective treatments of open wounds are poised to be needed by ever more patients worldwide.

Several of the serious treatment challenges facing a wound care clinician may derive from conflicting therapeutic approaches being required simultaneously to effectively treat an open wound. Two such significant conflicts are maintenance of wound site antiseptic sterility versus preservation of wound border skin microbiome functionality; and prevention of drying of the wound bed and/or of bordering perilesional tissue versus prevention of maceration. Achieving therapeutically optimized balances between such opposing clinical considerations is further complicated by the balances differing among wound types and, for a wound of a given type, changing with the wound's stage of healing.

Antiseptic Sterility vs Microbiome Functionality

Intact healthy skin normally presents against infection not only a mechanical barrier but also a bioactive barrier. Bioactivity is provided by commensal microbiota of the skin microbiome. The microbiota include numerous diverse types of viruses, fungi and bacteria. The latter constitute the bulk of the microbiome ecosystem. The microbiome ecosystem may differ and change according to body region characteristics (dry/moist/sebaceous) as well as according to degree of exposure to air and/or light.

By synthesizing and secreting specialized anti-microbial compounds, the skin microbiome biochemically thwarts attacks by agents of infection contacting the outer skin. And, as has become increasingly appreciated in the $21^{st}$ Century, the skin microbiome also dynamically affects lower-layer skin cells, modulating immunological and biosynthetic activities of dermal layers and also of hypodermal/subcutaneous layers, even as host cells reciprocally modify gene expression of the microbiota. (Harris-Tryon T A and Grice E A (2022) Microbiota and maintenance of skin barrier function. *Science* 376:940-945; Swaney M H and Kalan L R (2021) Living in Your Skin: Microbes, Molecules, and Mechanisms. *Infection and Immunity* 89 (4): e00695-20)

A lesion of the skin's mechanical barrier can give agents of infection access through the breach to exposed underlying tissue without the pathogens directly encountering the protective skin microbiome. In standard wound treatment practice, the lesion is, therefore, antiseptically cleansed and treated with antibiotics lethal to bacterial strains that cause infection, inclusive, inter alia, of *Staphylococcus aureus*. However, most antibiotics used in standard wound treatment practice also kill perilesional microbiome bacteria, inclusive, inter alia, of *Staphylococcus epidermidis* and *Cutibacterium acnes*, the predominant species of the microbiome bacterial component of most adult host body regions.

*Staphylococcus epidermidis* actively fights off *Staphylococcus aureus* by synthesizing and secreting antimicrobial molecules lethal to *S. aureus* but benign to the microbiome. Other *S. epidermidis* secretions are credited with inhibiting biofilm formation by *S. aureus*, such biofilms capable of shielding film-covered pathogens from anti-pathogen molecules. Additionally, *S. epidermidis* strengthens skin cell-to-cell junctions, both by its own secretions and by stimulation of underlying host dermal layers. During neonatal development and beyond, *S. epidermidis* primes host T leucocytes against *S. aureus* while training those immune cells to accept the presence and functioning of the microbiome. Host dermal and immune cells previously induced and promoted by *S. epidermidis* seem to be actively influenced by the microbiota's responses to a breach of skin with the lesion's attendant chemical signals from exposed underlying tissues; those influenced host cells are strongly implicated in contributing directly to wound healing. (Canchy L, Kerob D, et al. (2023) Wound healing and microbiome, an unexpected relationship. *J European Academy Dermatology Venereology* 37 (S3): 7-15; Linehan J L, Harrison O J, et al. (2018) Non-classical Immunity Controls Microbiota Impact on Skin Immunity and Tissue Repair. *Cell* 172:784-796)

*Cutibacterium acnes* metabolizes sebum secretions of the sebaceous areas that the bacillus is typically associated with, such as hair follicles. *C. acnes* metabolites include low pH products (e.g., propionic acid) that help keep free of infection the direct access-way between outer and inner skin layers afforded by the hair follicles. *C. acnes* has been shown effective against MRSA, methicillin-resistant *S. aureus* not treatable by front-line antibiotics. *C. acnes* secretions also inhibit biofilm formation by *S. epidermidis*, a condition associated with *S. epidermidis* pathogenicity. Reciprocally, *S. epidermidis* secretions can inhibit pathogenetic biofilm formation by *C. acnes*. *C. acnes* also induces and promotes host T helper ($T_H$) cells that play a direct role in wound antiseptic cleansing. (Thiboutot D M and Nelson A M (2021) Keeping the peace: commensal *Cutibacterium acnes* trains $CD4^+$ $T_H17$ cells to trap and kill. *J Clinical Investigation* 131(2): e145379)

Application of broad-spectrum antibiotics to a patient's wound site may be deadly to the microbiome bacterial population of perilesional skin adjacent the site. Losses to the skin microbiome bacteria disrupts the complexly balanced local microbiome ecosystem. Losses to population of *S. epidermidis* and/or *C. acnes* and attendant disruption of the skin microbiome ecosystem along the wound border, impair the ability of the patient's wound border cells to properly execute pre-programmed highly coordinated rehabilitative functions. Those functions include covering the site with newly formed daughter cells that migrate away from parent border cells, swimming along and through moist fibroblast surfaces that begin to overlay the wound bed in response to biochemical signals produced by site-local host cells and perilesional microbiota.

Some of those daughter cells migrating from wound border tissue respond to other biochemical signals contributed to by perilesional microbiota and by oxygen-starved wound site cells, and differentiate into nascent vascular endothelium cells. Those proto-vascular cells build new capillary beds to supply blood and, thereby, oxygen to the wound site's "under construction" replacement tissue.

Other cells migrating inward from the wound border differentiate into myofibroblast cells. These "muscle-like" cells coordinate to tug on the border and on the new skin cells, drawing the wound edges toward each other. The inward growing wound edges are pulled forward at rates and in concert with other concomitantly occurring cellular regrowth processes so as to foster scar-free wound closure.

Wound site cells and perilesional microbiota also produce biochemical signals that recruit macrophagic leukocytes to the wound site while simultaneously tamping down excess inflammation. The macrophages clean the wound site by attacking foreign invaders and eating away at and engulfing necrotic tissue, thus cleansing and debriding the site.

The above and other contributions of the perilesional microbiota to stages and processes of the body's highly coordinated healing responses are usually severely disrupted by the powerful antibiotics typically utilized in wound treatment to sterilize the wound site and prevent infection.

Accordingly, it would be desirable to provide compositions and methods of application of the same, that yield antiseptic conditions on and along the borders of the wound bed and keep the regions free of infection, but without causing severe disruption of the perilesional skin microbiome. Such a balance can be had by use of effective antibiotics that are not powerful broad-spectrum drugs.

However, effective antibiotics that are not powerful broad-spectrum drugs may prove insufficiently lethal to the wide variety of pathogenic bacteria that may assault the wound's exposed tissues. Accordingly, to increase the anti-microbial reach and power of the compositions, it would be desirable that the compositions' non-broad-spectrum microbiome-preserving antibiotics be complemented by multiple other microbiome-friendly anti-microbial components. It would be desirable that those components be select natural products having centuries-long track records of experience-based safe use on the skin. It would be desirable, also, that those components have been widely, successfully and safely used as anti-infection preservative agents, now known to be distinguished for their anti-microbial properties.

It would also be desirable that components of the compositions be multi-modally stimulative of the body's natural healing processes, such as neovascularization and metalloprotease biosynthesis, as well as acting as anti-microbials.

Drying vs Maceration

The wound site must be maintained moist to facilitate cell proliferation on the wound bed and along its perilesional borders, as well as to facilitate cellular migration along and through developing bed-covering biological surfaces. The proliferation and migration, coordinated with synchronized and targeted cellular differentiation, facilitate proper wound closure with limited scarring of and minimal functional loss to the repaired wound site. But excessive wetness, from exudate buildup and/or therapeutic application of aqueous treatments, may lead to tissues of the bed and borders becoming edematous and, thus, losing degrees of functionality required for healing. This concern may be heightened by such liquids being trapped on the wound site by an occlusive therapeutic covering. Yet occlusive coverings are needed to prevent evaporative drying of the wound site.

Accordingly, it would be desirable to provide separate compositions for the wetting and for the drying of open wounds, thereby giving the clinician fine-tuning control over the relative proportions of wetting and of drying for a given wound at its specific stage of healing. The wetting compositions could then be applied to clinician-assessed depths and breadths to the cleansed/prepared wound bed and borders. Following application, checking and, if needed, reapplication touch-ups of the wetting compositions to the clinician's satisfaction, the drying compositions could then be overlaid upon the wetting compositions to depths and breadths judged by the clinician to be optimal for the wound's drying until the next dressing change.

It would be desirable, also, that application of the wetting compositions facilitate formation of an occlusive cover over the wound bed and its immediately adjacent perilesional skin, but together with cover-penetrating non-aqueous anti-microbial/healing-promoting emollients. It would be desirable that some of the emollients should also be capable of transporting select therapeutic components of the overlying drying compositions through the occlusion cover to tissues of the wound bed and borders.

BRIEF DESCRIPTION OF THE DISCLOSURE

Compositions and methods for treatment of open wounds are provided that may yield antiseptic conditions on and along the borders of the wound bed, keeping the regions free of infection, but without causing severe disruption of the perilesional skin microbiome. The compositions and methods combine a two-part application protocol with well tolerated compounds that have been used safely and studied for decades; in many cases, for centuries. A mild antibiotic (relative to powerful broad-spectrum antibiotics) used as a wound disinfectant for over a century is provided in combination with natural products and natural-derived substances well known and long utilized in wound and/or skin treatment for their disinfectant properties and promotion of healing.

The two-part protocol uncouples emollient wetting of the wound bed and occlusive cover formation over the wound site from a closely following but separate step of applying drying/desiccating agents upon the occlusive cover. The degree of drying/desiccation relative to wetting of the wound may thus be set by the clinician at each dressing change over the course of wound healing to optimize the patient's clinical outcome.

The compositions and methods for open wound treatment provided herein take advantage of recently characterized immuno-regulatory properties of composition components. Leveraging these properties, as built into the method protocols of dual applications of composition components, may selectively promote natural healing processes—such as neovascularization, metalloprotease biosynthesis and macrophage recruitment—when most needed at various healing stages, while suppressing less desirable processes at most stages, such as inflammation.

The compositions and methods for open wound treatment provided herein may also utilize to good effect interactions among composition components. For example, one of the drying agents of the second part of the two-part protocol has low solubility in water, but is quite soluble in one of the emollients of the first part. This provides the drying agent a transport modality by which to cross the occlusive cover, and provides the covered wound bed with solubility products of the agent.

The compositions and methods for open wound treatment provided herein may also utilize to good effect synergies arising among composition components via protocol steps. For example, increased drying of the site contracts the wound bed, in turn raising the concentration of solubilized components, including those of drying agents, further desiccating the wound site. Of note is site-contraction increasing concentration of the antibiotic and, thereby, accelerating immuno-regulation by it of wound healing processes.

The compositions may be used to perform steps of the methods. The methods may include administration of the compositions to the wound site. The methods may include recurrent administration of the compositions to the wound site over a course of healing of the wound. The methods may include administration of the compositions to the wound by one or more than one wound clinician. The methods may include administration of the compositions to the wound by a first responder. The methods may include administration of the compositions to the wound by an untrained individual (such as a concerned citizen or even the wounded patient) with access to the compositions and use instructions, as may be had in an up-to-date first aid kit.

The compositions and methods disclosed herein have been utilized in clinical settings for treatment of open wounds of several types, including burns, diabetic ulcers and bed sores. The open wounds treated by the compositions and methods included open wound types often characterized as chronically non-healing/non-closing open wounds. Use of the compositions and methods has yielded clinically confirmed proper wound closure Technical effects of the compositions and methods, as confirmed over the many clinical cases of optimized wound healing following clinician application of the compositions and methods, include completed wound healing with minimal-to-no scarring of wound sites and patient satisfaction of functional recovery of the repaired tissue. Other aspects and advantages of the compositions and methods-including component amounts; and ease of execution of the two-part administration; as well as significant positive physiological and psychological benefits accruing to patients-will be further appreciated from the following detailed description.

DETAILED DESCRIPTION OF THE DISCLOSURE

Compositions and methods for treatment of open wounds are provided. The compositions may be used to perform steps of the methods. The methods may include administration of the compositions to a wound site.

The compositions may include and the methods may involve compositions of matter for therapeutic application to the wound site. The compositions may include a composition. The compositions may include a single composition. The compositions may include one or more than one composition.

The compositions may include a dry powder. The compositions may be formulated as a dry powder.

The compositions may be used in wound treatment in conjunction with a wound care ointment and/or cream. The ointment and/or cream may include high molecular weight (MW) non-water-soluble ingredients. The ointment and/or cream may include low MW non-water-soluble ingredients. The ointment and/or cream may include long-chain waxes. The ointment and/or cream may include mid-sized-chain oils. The ointment and/or cream may include short-chain lipids. The ointment and/or cream may include essential oils. The ointment and/or cream may include emollients. The ointment and/or cream may include anti-microbials. The ointment and/or cream may include any ingredient suitable for wound treatment ointments and/or creams.

The compositions may be used in wound treatment after application of the ointment and/or cream to a wound. The compositions may be used as a second step of a two-step wound care protocol. Spreading the ointment and/or cream on a properly cleansed wound bed may serve as a first step of the protocol. The ointment and/or cream may be spread to cover the wound bed. The ointment and/or cream may be spread to cover all the wound bed. The spread ointment and/or cream may cover also sides of the wound bed. The spread ointment and/or cream may cover also skin immediately bordering the wound bed.

The ointment and/or cream may be spread to overlay the wound bed. The ointment and/or cream may be spread to overlay all the wound bed. The spread ointment and/or cream may also overlie sides of the wound bed. The spread ointment and/or cream may overlie also skin immediately bordering the wound bed. The wound bed may be overlaid by the ointment and/or cream. The entire wound bed may be overlaid by the ointment and/or cream. The entire wound site may be overlaid by the ointment and/or cream.

The compositions may be applied onto the spread ointment and/or cream. The applied compositions may form a glaze upon the spread ointment and/or cream. The applied compositions may interact with the spread ointment and/or cream. Components of the compositions may be solubilized by ingredients of the ointment and/or cream.

Solubilized components of the compositions may transport to the overlaid wound bed and to its periphery. Solubilized components of the compositions may interact with the overlaid wound bed and with its peripheral tissue.

The compositions may include one or more than one antibiotic. The one or more than one antibiotic may be clinically demonstrated to immuno-regulate human cells.

The one or more than one antibiotic may be clinically demonstrated to promote leucocyte production of interleukins. The one or more than one antibiotic may be clinically demonstrated to promote leucocyte production of interleukin-12 (IL-12).

The one or more than one antibiotic may be clinically demonstrated to suppress leucocyte production of interleukins. The one or more than one antibiotic may be clinically demonstrated to suppress leucocyte production of interleukin-5 (IL-5). The one or more than one antibiotic may be clinically demonstrated to suppress leucocyte production of interleukin-6 (IL-6). The one or more than one antibiotic may be clinically demonstrated to suppress leucocyte production of interleukin-10 (IL-10).

The one or more than one antibiotic may include ethacridine lactate. Ethacridine lactate has been used as a wound disinfectant for over a century. Ethacridine is understood to intercalate between DNA bases of bacteria and, thereby, be disruptive of bacterial life functions.

Ethacridine lactate may be implicated in the immuno-regulation of leucocytes to promote production of IL-12. Ethacridine lactate may be implicated in the immuno-regulation of leucocytes to suppress production of IL-5, IL-6 and IL-10. (Reinhardt C S, Geske T, et al. (2005) A topical wound disinfectant (ethacridine lactate) differentially affects the production of immuno-regulatory cytokines in human whole-blood cultures *WOUNDS* 17 (8): 213-221)

Solubilized ethacridine lactate may be a source of lactate ions. Lactate ion is understood to be an angiogenesis signal. Lactate ion may serve to prompt neovascularization of the wound site. (Aslam R S, Scheuenstuhl H, et al. (2008) Lactate Controls Vascular Development in Wound Healing. *Wound Repair and Regeneration* 12 (2): A14)

Lactate ion may serve a anti-microbial function. (Alakomi H-L, Skytta E, et al. (2000) Lactic Acid Permeabilizes Gram-Negative Bacteria by Disrupting the Outer Membrane. *Applied and Environmental Microbiology* 66 (S): 2001-2005)

The concentration of ethacridine lactate in the dry powder may be in the range of about 0.1% to about 10% (wt/wt). The concentration of ethacridine lactate in the dry powder may be in the range of about 0.5% to 5% (wt/wt). The concentration of ethacridine lactate in the dry powder may be about 1% (wt/wt). The concentration of ethacridine lactate in the dry powder may not be greater than about 1% (wt/wt). The concentration of ethacridine lactate in the dry powder may not be less than about 1% (wt/wt). The concentration of ethacridine lactate in the dry powder may be any concentration suitable for wound treatment.

The one or more than one antibiotic may include nanoparticles of the one or more than one antibiotic. The nanoparticles of the one or more than one antibiotic may be of a variety of size ranges. The nanoparticles of the one or more than one antibiotic may be of any size range suitable for wound treatment.

The ethacridine lactate may include nanoparticles of ethacridine lactate. The nanoparticles of ethacridine lactate may be of a variety of size ranges. The nanoparticles of ethacridine lactate may be of any size range suitable for wound treatment.

The compositions may include at least one metal-containing species. The at least one metal-containing species may be clinically demonstrated to promote desiccation of the wound site. The at least one metal-containing species may be clinically demonstrated to promote reduction of the wound site dimensions.

The at least one metal-containing species may include zinc oxide (ZnO).

ZnO has a low solubility in water. Eugenol (derivable from cloves), an ingredient of the ointment and/or cream, may solubilize ZnO. Transport of eugenol-ZnO from above to below the overlying ointment and/or cream may bring eugenol, ZnO and/or Zn ion to the overlaid wound bed. Eugenol may be known for anesthetic properties. ZnO may be widely used as a drying agent. Zn ions are understood to modulate cellular process of wound healing. Zn ion is known for its anti-microbial properties. (Lin P-H, Sermersheim M, et al. (2018) Zinc in Wound Healing Modulation. *Nutrients* 10 (1). 16.) (Pasquet J, Chevalier Y, et al. (2014) The contribution of zinc ions to the antimicrobial activity of zinc oxide. *Colloids and Surfaces A* 457 (5) 263-274)

The concentration of ZnO in the dry powder may be in the range of about 0.5% to about 50% (wt/wt). The concentration of ZnO in the dry powder may be in the range of about 5% to about 20% (wt/wt). The concentration of ZnO in the dry powder may be about 10% (wt/wt). The concentration of ZnO in the dry powder may not be greater than about 10% (wt/wt). The concentration of ZnO in the dry powder may not be less than about 10% (wt/wt). The concentration of ZnO in the dry powder may be any concentration suitable for wound treatment.

The at least one metal-containing species may include nanoparticles of the at least one metal-containing species. The nanoparticles of the at least one metal-containing species may be of a variety of size ranges. The nanoparticles of the at least one metal-containing species may be of any size range suitable for wound treatment.

The ZnO may include nanoparticles of zinc oxide (nZnO). The nZnO nanoparticles may be of a variety of size ranges. The nZnO nanoparticles species may be of any size range suitable for wound treatment.

The compositions may include an excipient. The excipient may include corn starch. Corn starch is widely used as a drying agent.

The compositions may include and the methods may involve a powder for therapeutic application to the wound site. The powder may include a dry powder.

The powder may include an antibiotic. The antibiotic may be clinically demonstrated to immuno-modulate behavior of leucocytes.

The antibiotic may be clinically demonstrated to suppress production of interleukin species that promote inflammation. The antibiotic may be clinically demonstrated to immuno-modulate behavior of epithelial cells, such as those bordering the wound site, to proliferate.

The antibiotic may include ethacridine lactate.

The concentration of ethacridine lactate in the powder may be in the range of about 0.1% to about 10% (wt/wt). The concentration of ethacridine lactate in the powder may be in the range of about 0.5% to 5% (wt/wt). The concentration of ethacridine lactate in the powder may be about 1% (wt/wt). The concentration of ethacridine lactate in the powder may not be greater than about 1% (wt/wt). The concentration of ethacridine lactate in the powder may not be less than about 1% (wt/wt). The concentration of ethacridine lactate in the powder may be any concentration suitable for wound treatment.

The antibiotic may include nanoparticles of the antibiotic. The nanoparticles of the antibiotic may be of a variety of size ranges. The nanoparticles of the antibiotic may be of any size range suitable for wound treatment.

The ethacridine lactate may include nanoparticles of ethacridine lactate. The nanoparticles of ethacridine lactate may be of a variety of size ranges. The nanoparticles of ethacridine lactate may be of any size range suitable for wound treatment.

The powder may include at least one metal-containing species. The at least one metal-containing species may include a metal-containing species.

The metal-containing species may directly and/or indirectly improve wound healing.

The metal-containing species may be clinically demonstrated to contribute to contraction of the wound site. The metal-containing species may effect the contraction via physio-chemical processes. The metal-containing species may effect the contraction via modulation of cellular activity.

The metal-containing species may be clinically demonstrated to contribute to positive modulation of immune function responses that are protective against microbial attack. The metal-containing species may promote recruitment of macrophages to the wound site. The metal-containing species may support macrophage function at the wound site.

The metal-containing species may provide cofactors for cellular biosynthesis of enzymes. The enzymes may be needed for maintenance of cellular function. The enzymes may include metalloproteases. The metalloproteases may serve intra-and/or extra-cellular functions. The intra-and/or extra-cellular functions may include anti-microbial functions. The metal-containing species may include zinc oxide (ZnO).

The concentration of ZnO in the powder may be in the range of about 0.5% to about 50% (wt/wt). The concentration of ZnO in the powder may be in the range of about 5% to about 20% (wt/wt). The concentration of ZnO in the powder may be about 10% (wt/wt). The concentration of ZnO in the powder may not be greater than about 10% (wt/wt). The concentration of ZnO in the powder may not be less than about 10% (wt/wt). The concentration of ZnO in the powder may be any concentration suitable for wound treatment.

The metal-containing species may include nanoparticles of the metal-containing species. The nanoparticles of the metal-containing species may be of a variety of size ranges. The nanoparticles of the metal-containing species may be of any size range suitable for wound treatment.

The ZnO may include nanoparticles of zinc oxide (nZnO). The nZnO nanoparticles may be of a variety of size ranges. The nZnO nanoparticles species may be of any size range suitable for wound treatment.

The powder may include an excipient. The excipient may include corn starch.

The methods may include a method of treating a wound. The method may utilize the compositions.

The method may include preparing a surface of the wound. The preparing may include one or more standard procedures for preparing a wound surface for treatment. Those procedures may include: debridement, exudate removal, and rinsing with a wash that is sterile and/or antiseptic.

The method may include spreading an emollient on the prepared surface. The emollient may be a clinically demonstrated therapeutically effective antimicrobial emollient.

The spreading may form a cover over the surface. The cover may extend over all the wound, including perilesional tissue.

The method may include applying a dry powder formulation upon the cover. The method may include applying the dry powder formulation onto the emollient. The dry powder may interact with the emollient. Components of the dry powder may be solubilized by ingredients of the emollient. The applied dry powder may form a glaze upon the cover.

The applying may include distributing the dry powder upon the cover. The distributing may be aided by an appropriate hand-held tool. The applying may include sprinkling the dry powder onto the cover. The applying may include shaking the dry powder onto the cover. The applying may include any means of covering the emollient that is consistent with wound treatment and clinical/situational safety standards.

The emollient, which may include eugenol, may be included in a mixture that includes long-chain waxy esters. On average, the long chain waxy esters may have higher MWs than MWs of the emollient. The mixture may include long-chain polyunsaturated hydrocarbons. On average, the long chain polyunsaturated hydrocarbons may have higher MWs than MWs of the emollient. The mixture may include high MW non-water-soluble ingredients. The mixture may include low MW non-water-soluble ingredients.

The eugenol may be mixed into the mixture. After the applying, the eugenol may migrate out of the mixture. The eugenol may migrate above the cover into the dry powder. The eugenol may migrate below the cover to the prepared surface. The eugenol may transport solubilized components of the applied dry powder from above the cover to below the cover, making those solubilized components available to the wound bed and perilesional tissues.

The dry powder may include an antibiotic. The antibiotic may include ethacridine lactate.

The dry powder may include at least one metal-containing species. The at least one metal-containing species may include zinc oxide (ZnO).

The dry powder may include an excipient. The excipient may include cornstarch.

According to the method, prior to applying the dry powder upon the cover, an assessment is to be made as to the amount of dry powder to be applied. While a general rule of thumb may be that high moistness may require application of "more" dry powder, while low moistness may require application of "less" dry powder, realistic clinical assessment may be more sophisticated, taking into account factors besides moistness. The assessment may include consideration of such wound conditions as: wound type and/or wound severity and/or the current stage of healing of the wound and/or levels of moistness of the wound and/or overall condition of the patient. Wound type may include one or more of burn, ulcer, sore, excision and laceration.

Initial studies of use of the compositions and methods presented herein on human subjects are underway, in tandem with porcine burn studies. The initial human studies have yielded wound closure with minimal-to-no scarring and with patient/clinician satisfaction regarding functionality of repaired tissue.

Expanded human studies are planned, expected to focus on use of the compositions and methods disclosed herein to wound treatment.

All references cited in the present application are incorporated in their entirety herein by reference to the extent not inconsistent herewith.

Thus, compositions and methods for wound treatment have been provided. Persons skilled in the art will appreciate that the present invention can be practiced by other than the described embodiments, which are presented for purposes of illustration rather than of limitation. The present invention is limited only by the claims that follow.

What is claimed is:

1. A treatment for therapeutic application to a wound site, the treatment comprising:

a drying composition including:

an antibiotic including ethacridine lactate, said antibiotic clinically demonstrated to:

promote leucocyte production of interleukin-12 and suppress leucocyte production of interleukin-10; and at least one metal-containing species clinically demonstrated to promote:

desiccation of the wound site and reduction of wound site dimensions; and a wetting composition forming, when applied to a wound bed of the wound site, an occlusive wound cover;

wherein:

the wetting composition, comprising waxy esters and eugenol, is applied upon the wound bed;

the drying composition is applied upon the occlusive wound cover formed via the waxy esters, the occlusive cover providing transport therethrough of solubilized components of the drying composition, the transport making the at least one metal-containing species available to the underlying wound bed, the transport configured to promote wound bed desiccation;

the at least one metal-containing species includes zinc oxide (ZnO); and the eugenol solubilizes the components of the drying composition.

2. The treatment of claim 1 wherein a concentration of ethacridine lactate in the drying composition is in a range of about 0.1% to about 10% (wt/wt).

3. The treatment of claim 1 wherein a concentration of ethacridine lactate in the drying composition is about 1% (wt/wt).

4. The treatment of claim 1 wherein a concentration of ZnO in the drying composition is in a range of about 0.5% to about 50% (wt/wt).

5. The treatment of claim 1 wherein a concentration of ZnO in the drying composition is about 10% (wt/wt).

6. The treatment of claim 1 wherein the antibiotic includes nanoparticles of the antibiotic.

7. The treatment of claim 1 wherein the at least one metal-containing species includes nanoparticles of the metal-containing species.

8. The treatment of claim 1 wherein the drying composition further includes an excipient.

9. The treatment of claim 8 wherein the excipient includes corn starch.

10. A treatment for therapeutic application to a wound site, the treatment comprising:

a powder including:

an antibiotic including ethacridine lactate, said antibiotic clinically demonstrated to immuno-modulate behavior of leucocytes to suppress production of interleukin species that promote inflammation;

at least one metal-containing species clinically demonstrated to contribute to contraction of the wound site; and an excipient; and an ointment and/or cream including:

an emollient-rich mixture of non-water-soluble ingredients comprising waxy esters and eugenol, wherein:

the ointment and/or cream is applied upon a wound bed of the wound site, forming, via the waxy esters, an occlusive cover over the wound bed;

then the powder is applied upon the occlusive cover, the occlusive cover providing transport therethrough of solubilized components of the powder, making the solubilized components available to the wound bed;

the solubilized components of the powder include the at least one metal-containing species that, transported through the occlusive cover to the wound bed, contributes to contraction of the wound bed of the wound site;

the at least one metal-containing species includes zinc oxide (ZnO); and the eugenol solubilizes and transports the components of the powder.

11. The treatment of claim 10 wherein the powder includes a dry powder.

12. The treatment of claim 10 wherein a concentration of ethacridine lactate in the powder is in a range of about 0.1% to about 10% (wt/wt).

13. The treatment of claim 10 wherein a concentration of ethacridine lactate in the powder is about 1% (wt/wt).

14. The treatment of claim 10 wherein a concentration of ZnO in the powder is in a range of about 0.5% to about 50% (wt/wt).

15. The treatment of claim 10 wherein a concentration of ZnO in the powder is about 10% (wt/wt).

16. The treatment of claim 10 wherein the antibiotic includes nanoparticles of the antibiotic.

17. The treatment of claim 10 wherein the at least one metal-containing species includes nanoparticles of the metal-containing species.

18. The treatment of claim 10 wherein the excipient includes corn starch.

19. The treatment of claim 10 wherein the at least one metal-containing species is further clinically demonstrated to contribute to positive modulation of immune function responses that are protective against microbial attack.

20. A method of treating a wound, comprising:

preparing a surface of the wound, such preparing including one or more of debridement, removal of exudate, or rinsing with sterile and/or antiseptic wash;

spreading on the prepared surface an emollient-rich mixture of non-water-soluble ingredients including:

at least one clinically demonstrated therapeutically effective antimicrobial emollient; and waxy esters;

forming, via the waxy esters, an occlusive cover over the wound;

applying onto the occlusive cover a dry powder formulation that includes:

at least one metal-containing species clinically demonstrated to promote wound desiccation; and an excipient; and providing solubilized components of the dry powder to the prepared surface via transport through the occlusive cover to the covered prepared surface, the solubilized components including the at least one metal-containing species, thereby promoting wound desiccation of the prepared surface;

wherein:

the at least one antimicrobial non-water-soluble emollient includes eugenol;

the at least one metal-containing species includes zinc oxide (ZnO), and the applying follows an assessment of an amount of dry powder to apply, the assessment including consideration of at least one of the wound's:

type, severity, stage of healing, or moistness level.

21. The method of claim 20 wherein the dry powder formulation further includes an antibiotic including ethacridine lactate.

22. The method of claim 20 wherein the type of the wound includes one or more of: burn, ulcer, original sore, excision or laceration.

23. The treatment of claim 1 wherein the occlusive cover provides transport therethrough of the antibiotic.

24. The method of claim 20 further comprising, before the providing:

migrating out of the mixture the at least one non-water-soluble clinically demonstrated therapeutically effective antimicrobial emollient; and then solubilizing the components of the dry powder in the at least one non-water-soluble clinically demonstrated therapeutically effective antimicrobial emollient migrated out of the mixture.

* * * * *